United States Patent [19]

Uchida et al.

[11] Patent Number: 5,294,522
[45] Date of Patent: Mar. 15, 1994

[54] PHOTOCHROMIC COMPOUND

[75] Inventors: Manabu Uchida, Onojoshi; Masahiro Irie, Kasugashi, both of Japan

[73] Assignee: Chisso Corporation, Osaka, Japan

[21] Appl. No.: 25,133

[22] Filed: Mar. 2, 1993

[30] Foreign Application Priority Data

Mar. 5, 1992 [JP] Japan ................... 4-083379

[51] Int. Cl.$^5$ .................. G03C 1/73; C07D 333/50
[52] U.S. Cl. ........................... 430/345; 430/19;
430/332; 430/339; 430/343; 430/962; 252/586;
548/418; 548/427; 549/41; 549/45; 549/46;
549/47; 549/48; 549/61; 549/81; 549/82;
549/83; 549/381; 549/382; 549/388
[58] Field of Search ............... 430/1, 19, 332, 339,
430/343, 345, 962; 252/586; 549/41, 45, 46, 47,
48, 61, 71, 79, 80, 81, 82, 83, 381, 382, 388, 390;
548/418, 427

[56] References Cited

U.S. PATENT DOCUMENTS 5,234,799  8/1993  Nagai et al. ................. 430/19

OTHER PUBLICATIONS

CA78(3):15971b, Jan. 1973.
CA118(13):123863w, Mar. 1993.
CA118(19):187424m, May 1993.

Primary Examiner—Hoa Van Le
Attorney, Agent, or Firm—Fred Philpitt

[57] ABSTRACT

A novel photochromic compound as a photoreactive material making use of photochromism is provided, which compound is expressed by the following formula (1) or (2):

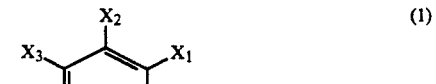

or

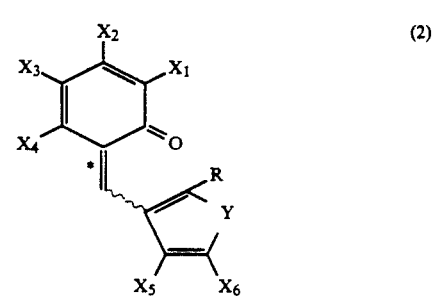

wherein R is alkyl, alkoxy, perfluoroalkyl or cyano; $X_1$, $X_2$, $X_3$, $X_4$, $X_5$ and $X_6$ are each H, halogen, alkyl, alkoxy, cyano, alkanoyloxy or alkyloxycarbonyl, or a substituted or unsubstituted benzene ring is formed by condensation between at adjacent groups among $X_1$ to $X_6$; Y is $Y_1C=CY_2$, O, S, SO, $SO_2$ or $NY_3$ wherein $Y_1$ and $Y_2$ are each as defined in the case of the above $X_1$ to $X_6$ and $Y_3$ is H, alkyl, alkanoyl, alkyloxycarbonyl or aryl; and the symbol ∼∼ refers to occurrence of E- or Z-isomer, and which compound is useful as rewritable optical memory element or photo-display element and also as solar energy-storage material, duplicating material, masking material, optical filter, toys, etc.

2 Claims, 3 Drawing Sheets

PHOTOCHROMIC COMPOUND

BACKGROUND OF THE INVENTION

1. Field of the Invention

This invention relates to a photoactive material making use of photochromism. More particularly it relates to a photochromic compound expressed by the formula (I) or its precursor expressed by the formula (II), the respective formulas being described below

2. Description of the Related Art

In recent years, with rapid development of information industries, high density memory media have been required. Optical data storage media have a possibility of remarkably surpassing magnetic data storage media employed so far, in the aspect of memory density; hence a number of researches have been carried out. Optical media include that of Write Once type wherein a recording is possible only once and that of Rewritable type wherein reversible recordings are possible, and photochromic compounds belong to materials employed as the latter Rewritable type optical media.

Photochromic compounds refer to a compound which changes the spectrum by irradiating a light of a certain wavelength and returns to the original spectra by heat or irradiation of a light of another wavelength. When such photochromic compounds are intended to be applied to optical memory media, a photochromic compound which does not fade thermally at room temperature is required for an archival storage. An example of such a compound is disclosed in M. Irie, Jpn. J. Appl. Phys., 28 supple 28-3, 215 (1989).

However, as to such a photochromic compound,- since the molecules are isomerized in proportion to the number of photons absorbed in principle, the media employing the compound have a drawback that even a very weak light employed for reading erases the memory gradually.

Further, photochromic compounds are characterized in that they change the colors by photoirradiation; thus it has been proposed that the compounds can be utilized for display elements. In this case, too, a drawback has been raised that the display fades out in ordinary sunlight or electric light.

As a method for preventing such a record and display from breaking, several methods have been proposed. A method is to use thermal threshold in the photochromic reaction of J-aggregates of spirobenzopyrans. The photochromic reactions depend on the laser light intensity. When the light intensity is high enough to heat the media above the threshold temperature, fading of color proceeds, while the fading is suppressed with a weak laser light. Non-destructive read-out more than 1,000 times was achieved by using the method (J. Hibino, Basic Technologies for Future Industries, the 3rd Symposium on Photonic Materials, Extended Abstracts, p165(1992)). Another method is to read the memory by two lasers with different wavelengths, in which diarylethenes with gated photochemical reactivity were used as the media (M. Irie et al., Optical Memory Symposium'92 (1992)). Physical property changes of liquid crystals by the photochromic reactions were also used as the stable memory, which can be read without destruction with the laser light which can not induce the photochromic reactions (K. Ichimura, Kagaku to Kogyo, 43,783(1992)). All of these methods, however, have drawbacks, such that the heating causes the degradation of the media and they need more than three lasers.

It is known that the efficiency of the photoisomerization is light-intensity dependent (J. Chem. Soc. Perkin Trans 2, 873, 1991), but according to the example, even when the light intensity is very weak, the photoreaction proceeds to some extent; hence it is impossible to completely overcome non-destructive read-out. Further, since another isomer is unstable, it is difficult to store the memory and display for a long time, and change in the absorption spectra are poor.

The present inventors have made extensive research to find out a photochromic compound which is possible to solve the above-mentioned problems. As a result, we have found a photochromic compound which does not isomerize when the light intensity is weak, but isomerizes only when the intensity is strong, and thus have completed the present invention.

As apparent from the foregoing, the object of the present invention is to provide a photochromic compound that recordings do not fade out in the reading process and are thermally stable, and a photochromic medium using the compound.

SUMMARY OF THE INVENTION

The present invention has the following constitutions (1) to (4):

(1) A photochromic compound expressed by the formula (1)

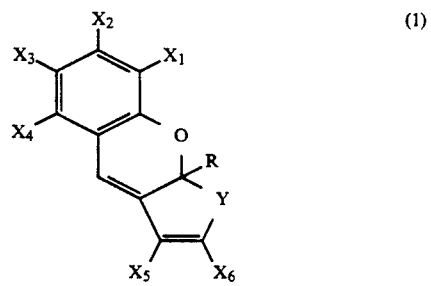

wherein R represents alkyl group, alkoxy group, perfluoroalkyl group or cyano group and $X_1$, $X_2$, $X_3$, $X_4$, $X_5$ and $X_6$ each independently represent hydrogen atom, halogen atom, alkyl group, alkoxy group, cyano group, alkanoyloxy group or alkyloxycarbonyl group, a substituted or unsubstituted benzene ring is formed by condensation between at $X_1$ and $X_2$, or/and between at $X_3$ and $X_4$, or/and between at $X_5$ and $X_6$; and Y represents $Y_1C=CY_2$, O, S, SO, $SO_2$, or $NY_3$ wherein $Y_1$ and $Y_2$ each independently represent hydrogen atom, halogen atom, alkyl group, alkoxy group, alkanoyloxy group or alkyloxycarbonyl group, or a substituted or unsubstituted benzene ring is formed by condensation between at $Y_1$ and $Y_2$ and $Y_3$ represents hydrogen atom, alkyl group, alkanoyl group, alkyloxycarbonyl group or aryl group.

(2) A compound as a precursor of the compound of item (1), expressed by the formula (II)

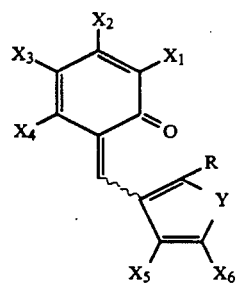

(2)

wherein R represents alkyl group, alkoxy group, perfluoroalkyl group or cyano group and $X_1$, $X_2$, $X_3$, $X_4$, $X_5$ and $X_6$ each independently represent hydrogen atom, halogen atom, alkyl group, alkoxy group, cyano group, alkanoyloxy group or alkyloxycarbonyl group, or a substituted or unsubstituted benzene ring is formed by condensation between at $X_1$ and $X_2$, or/and between at $X_3$ and $X_4$, or/and between at $X_5$ and $X_6$; Y represents $Y_1C=CY_2$, O, S, SO, $SO_2$ or $NY_3$ wherein $Y_1$ and $Y_2$ each independently represent hydrogen atom, halogen atom, alkyl group, alkoxy group, alkanoyloxy group or alkyloxycarbonyl group, or a substituted or unsubstituted benzene ring is formed by condensation between at $Y_1$ and $Y_2$ and $Y_3$ represents hydrogen atom, alkyl group, alkanoyl group, alkyloxycarbonyl group or aryl group; and the symbol ～ refers to occurrence of E- or Z-isomer.

(3) A photochromic medium containing a photochromic compound set forth in item (1).
(4) A medium containing a compound set forth in item (2).

DETAILED DESCRIPTION OF PREFERRED EMBODIMENTS

In the above formula (1) and (2), examples of substituents on the substituted benzene formed by condensation between at $X_1$, $X_2$, $X_3$, $X_4$, $X_5$, $X_6$ and $Y_1$ and $Y_2$ are halogen atom, alkyl group, alkoxy group, alkanoyloxy group, aryl group, nitro group, amino group, cyano group, carboxyl group, alkyloxycarbonyl group, etc., and one or more of these substituents may be attached on the benzene ring.

Concrete examples of the photochromic compound of the present invention are as follows (R and $Y_3$ in the formulas mentioned below are as defined above):

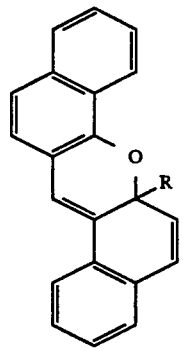

(1a)

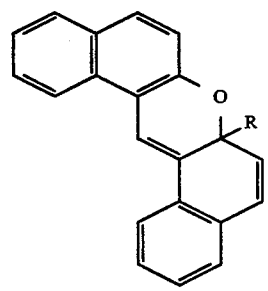

(1b)

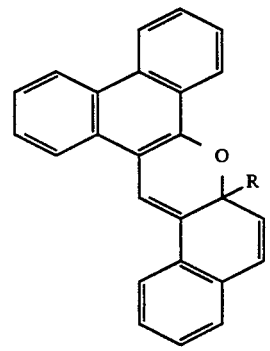

(1c)

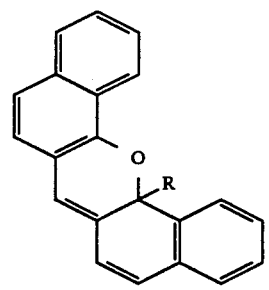

(1d)

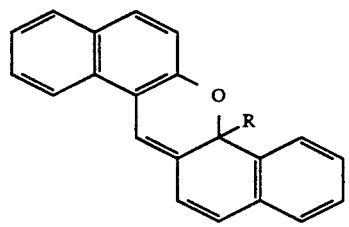

(1e)

(1f)
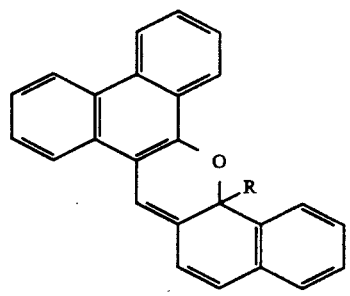
(1k)
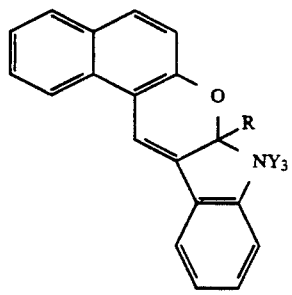
(1g)
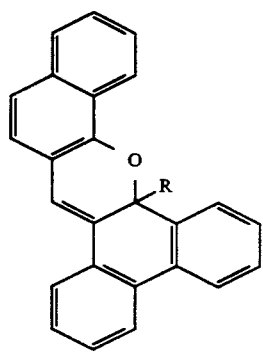
(2a)
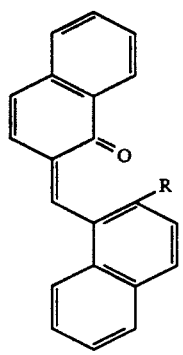
(1h)
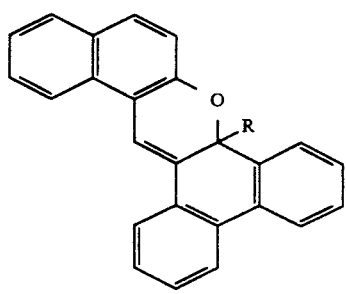
(2b)
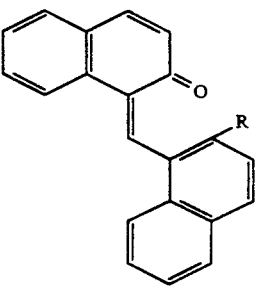
(1i)
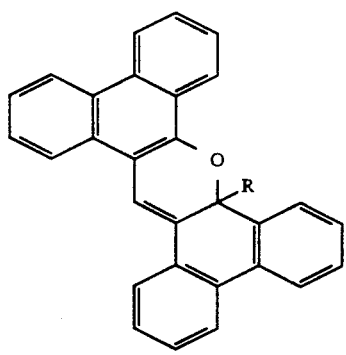
(2c)
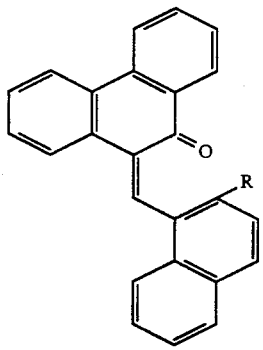
(1j)
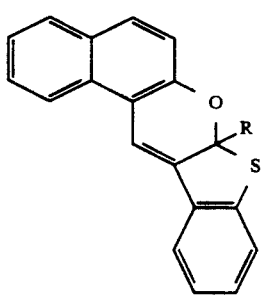
(2d)
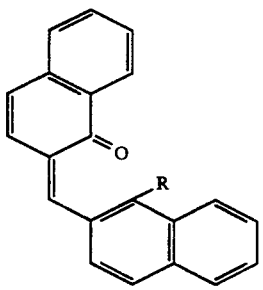

-continued

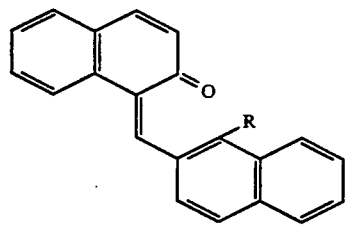 (2e)

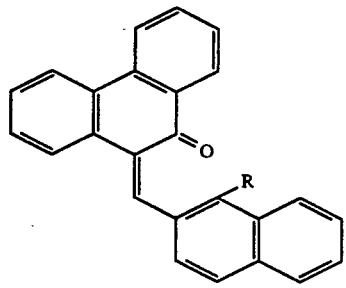 (2f)

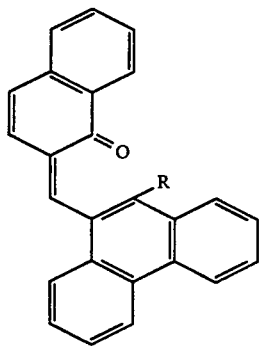 (2g)

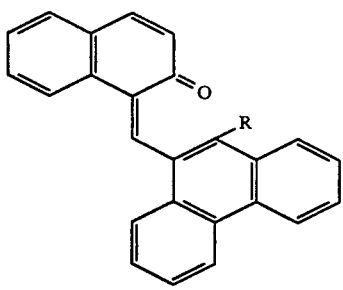 (2h)

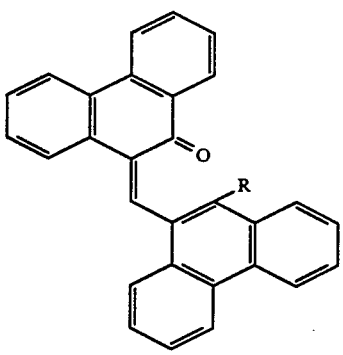 (2i)

-continued

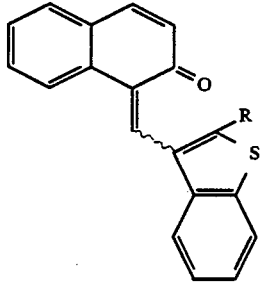 (2j)

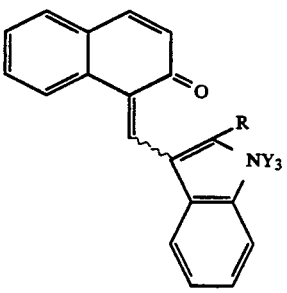 (2k)

The compound of the present invention is well soluble in general organic solvents such as hexane, toluene, chloroform, ether, acetone, ethanol, ethyl acetate, etc. Further, since the compound&of the present invention have a good compatibility with general polymers, it is possible to uniformly disperse them in the polymers. Examples of such polymers are polyolefins, polystyrene, polycarbonates, PMA, PET, etc.

Figure 1:
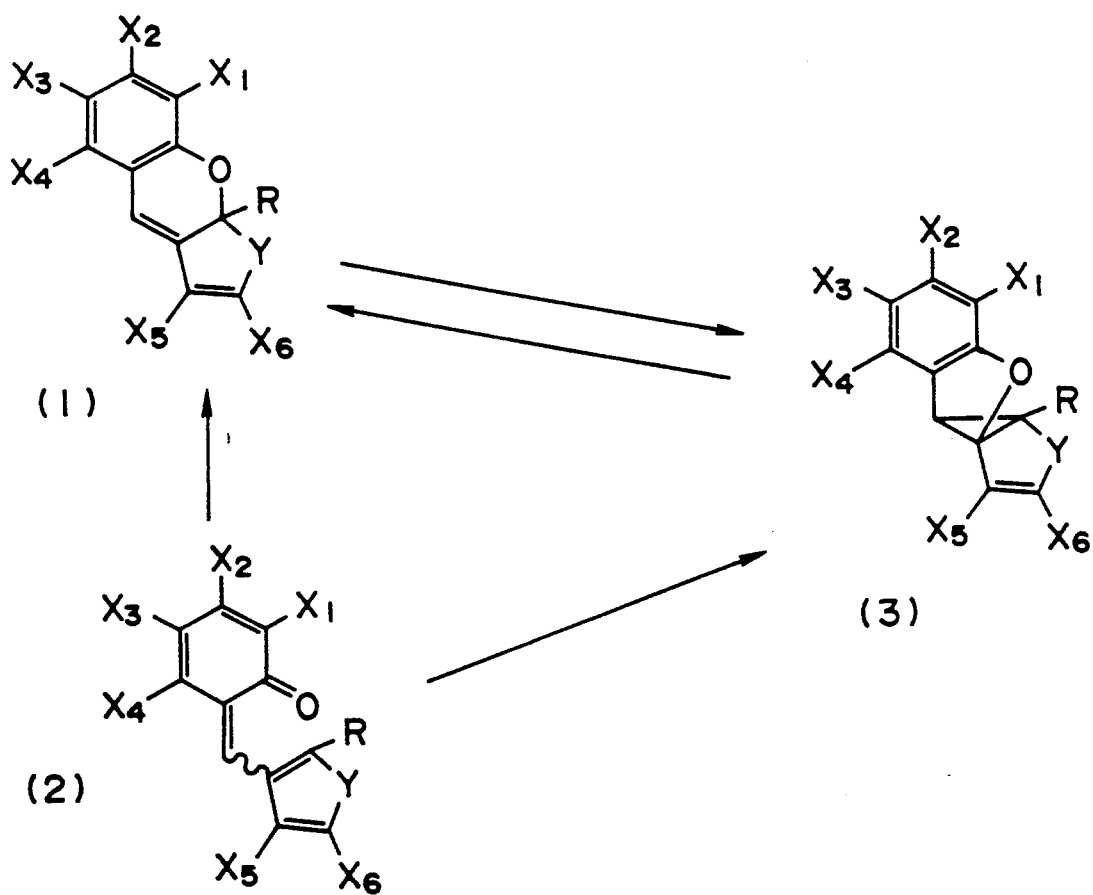
FIG. 1 illustrates the reaction formulas of photochromic reactions.
Figure 2:
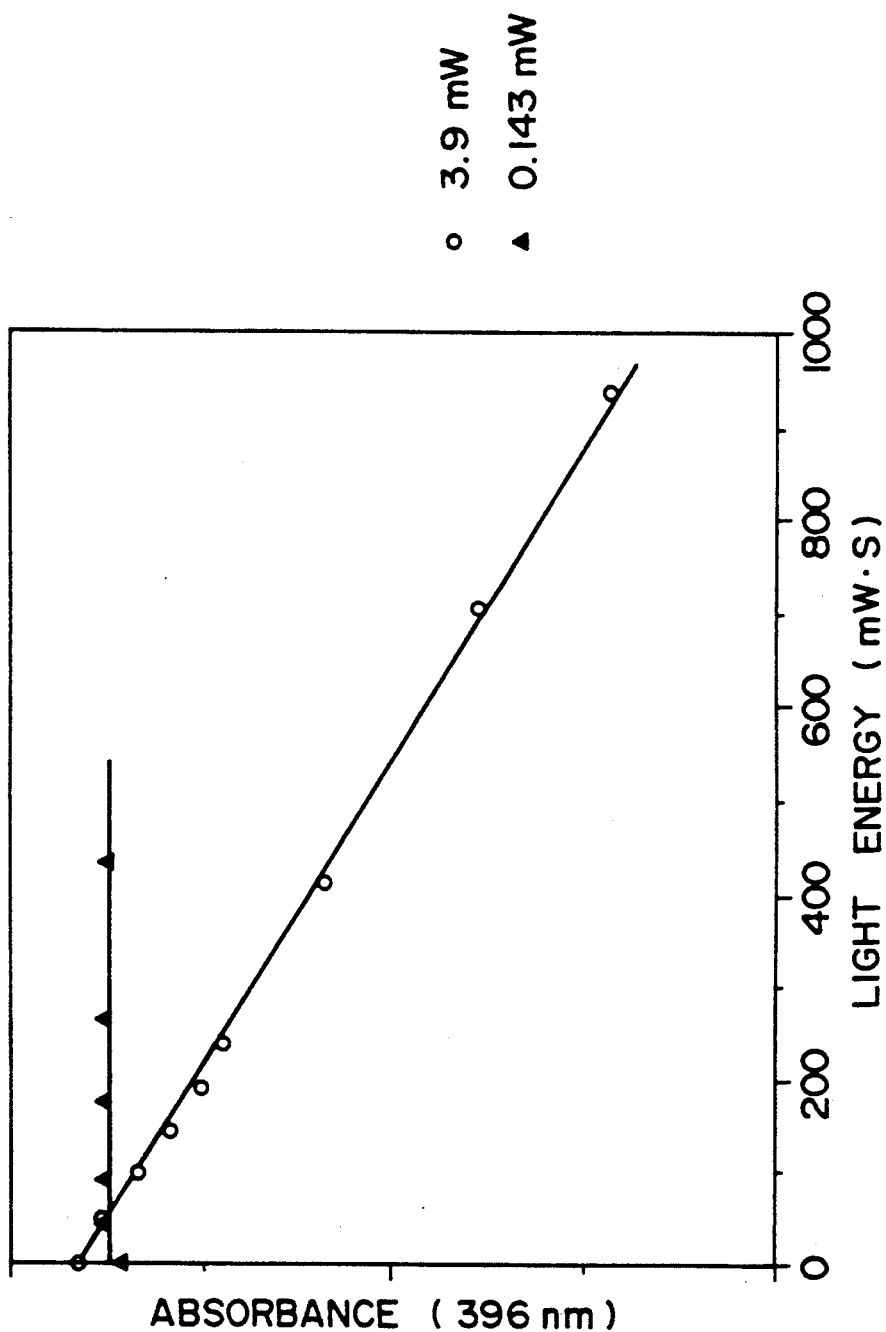
FIG. 2 illustrates a light intensity-dependency in a photoreaction from isomer 1 into isomer 3.
Figure 3:
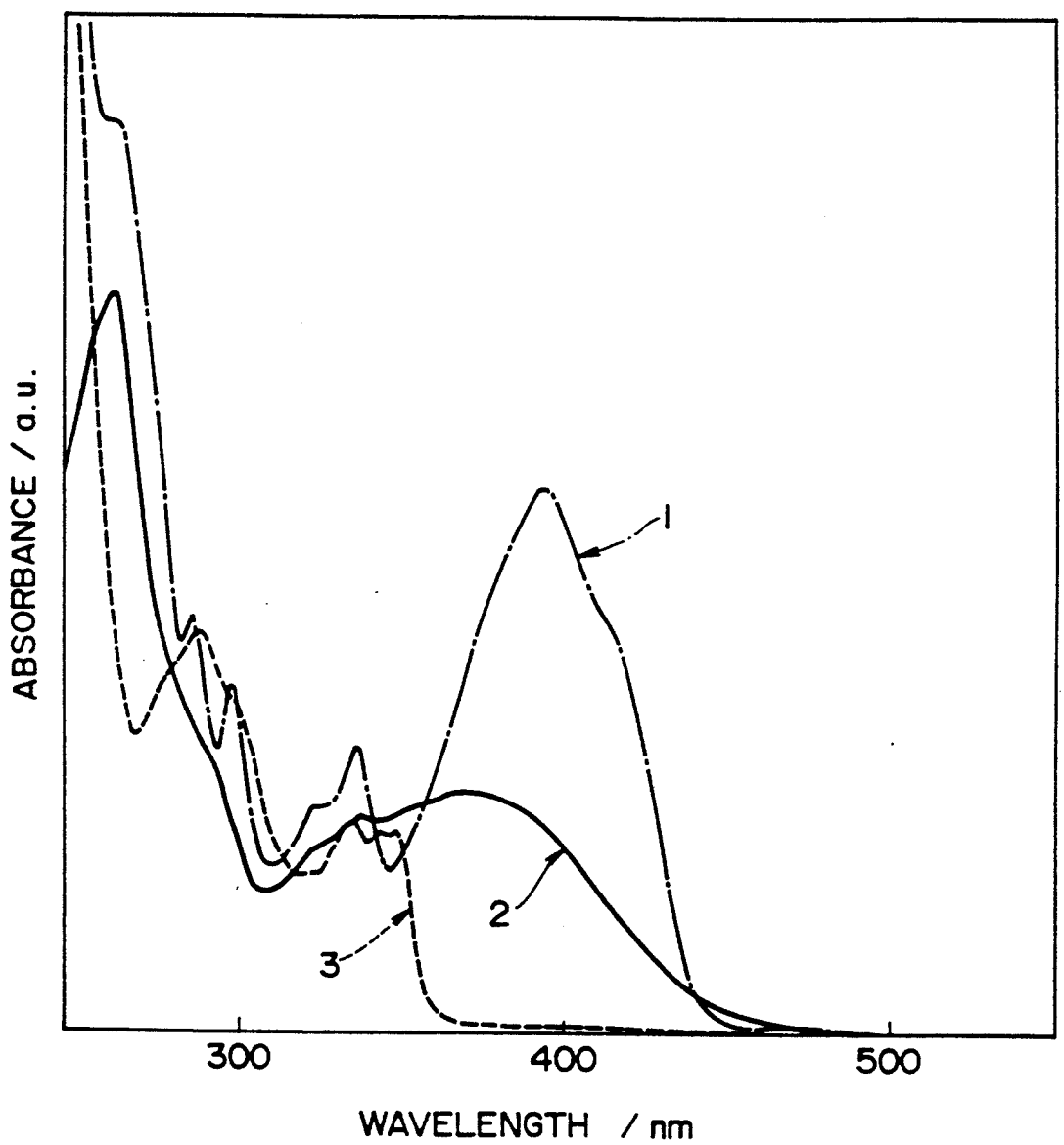
FIG. 3 illustrates the absorption spectra of 14aH-14a-methylbenzo[f]naphtho[3,2]chromene prepared in Example 1,
wherein numeral 1 represents the spectra of compound expressed by the formula 1 (after irradiated by UV light),
numeral 2 represents the spectra of compound expressed by the formula 2 and
numeral 3 represents the spectra of compound after irradiated by visible light.

In such a medium, compound 1 of the present invention undergoes a photochromic reaction as shown in FIG. 1, and the reaction from 1 into 3 does not proceed when the light intensity is weak, while the reaction proceeds when the intensity is strong. On the other hand, compound 2 is a precursor of compound 1 and compound 3, and when a light is irradiated onto compound 2, if the light intensity is weak, it isomerizes into compound 1, while if the intensity is strong, it isomerizes into compound 3. Change in the absorption spectra of compound 1a among the compounds of the present invention is shown in FIG. 3.

Since both the isomers (1 and 3) are thermally stable, they are suitable as one component of optical storage media or display media. Further, since the reaction from 1 to 3 depends on a light intensity, non-destructive read-out of memory and display is possible.

The colorless form of the compound of the present invention has a three-membered structure having a high strain energy; hence it is suitable to a component of solar energy-storage material which can transform solar energy into chemical energy and take out it in necessity.

Further, the compound of the present invention has a very high transformation efficiency into other isomers by way of photoreaction, that is, the transformation efficiency from 1a to 3a is 100% and that from 3a to 1a is 99% or higher. This fact leads to making higher the sensitivity or contrasting of optical memory element or photodisplay element.

Besides these use applications, the compound has broad use applications, that is, it is usable for optical filter, masking material, actinometer, decorative material, omoshiro goods ("omoshiro": a Japanese term meaning "amusing"), etc.

Next, the preparation process of the compound of the present invention will be illustrated below.

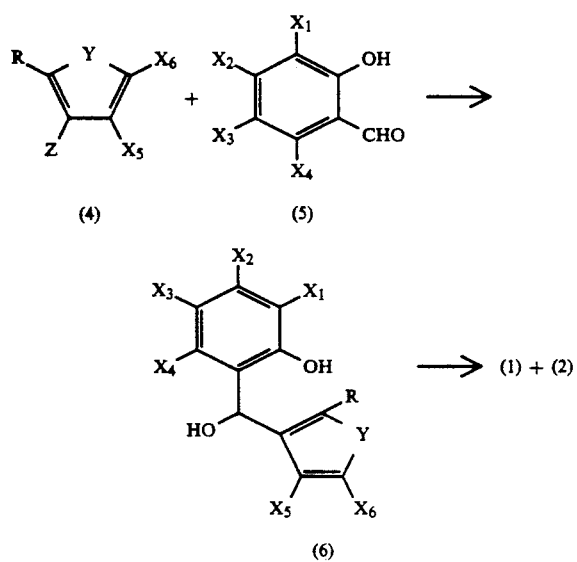

In the above formulas, $X_1$, $X_2$, $X_3$, $X_4$, $X_5$, $X_6$, Y and R are as defined above and Z represents Li, $MgZ_1$ (wherein $Z_1$ represents Cl, Br or I), $ZnZ_1$ or $SnZ_1$.

Namely, an organometallic compound of the formula (4) which can be prepared by usual halogen-metal exchange is reacted with a salicylaldehyde derivative (5) to obtain a diol compound (6). The solvent used at the time has no particular limitation as far as it is an inert solvent, but an ether solvent such as ether, tetrahydrofuran, etc. is preferred. The reaction temperature has no particular limitation, and the reaction can be carried out within $-100°$ to $250°$ C.

Next, the resulting diol compound (6) is reacted with a dehydration catalyst such as magnesium sulfate, sodium sulfate, molecular shieve, silica gel, $P_2O_5$, etc. to obtain the compounds of the present invention (1) and (2). The reaction is accelerated by an acidic catalyst such as p- toluenesulfonic acid, etc and by heating. The reaction temperature has no particular limitation, but it is preferred to fall within a range of $0°$ to $200°$ C.

Next, the photochromic medium of the present invention will be described.

Examples of a process for mixing a photochromic compound of the present invention within a medium are vacuum deposition process, spin-coating process, coating process, casting process, etc. Examples of the medium used herein are paper, glass, silica, plastics, metals, etc. The shape of such medium has no particular limitation, and if necessary, it may be finely-divided particles, etc.

When the photochromic medium thus prepared is exposed to a light of a wavelength causing the photochromic reaction, memory or display can be effected. The light source employed for the memory or display may be general-purpose ones such as mercury lamp, xenon lamp, laser, etc. The light used for the recordings is preferred to be a light having a high intensity and falling within a range of $10^{-5}W/cm^2$ to $1$ $W/cm^2$ although it varies depending upon materials.

Further, the read-out light is preferred to be a light having a low intensity and falling within a range of $10^{-3}W/cm^2$ to $10^{-8}$ $W/cm^2$ although it varies depending upon materials. In the display, the kind of the light has no particular limitation, and even when usual electric light or sunlight is employed, erasion of display by the light is not observed.

EXAMPLE

Next, the present invention will be described in more detail by way of Examples, but it should not be construed to be limited thereto.

Example 1

Preparation of 14aH-14a-methylbenzo[f]naphtho[3,2]chromene

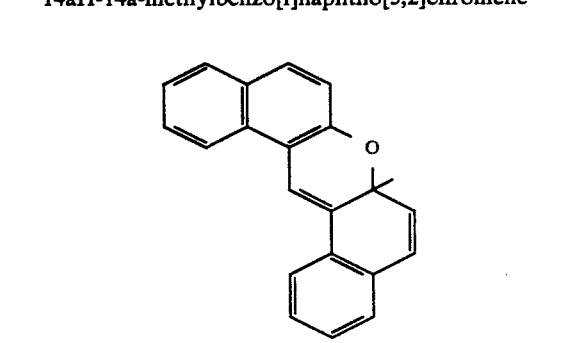

1-Bromo-2-methylnaphthalene (442 mg) and THF (5 ml) were placed in a 50 ml capacity three-neck flask, followed by cooling them down to $0°$ C., then dropwise adding a hexane solution (1.6 ml) of 1.6N n-butyllithium, agitating the mixture at room temperature for 15 minutes, adding a THF solution (5 ml) of 2-hydroxy-1-naphthaldehyde (172 mg), agitating the mixture for 5 hours, adding water (20 ml) and ether (20 ml) for extraction, twice washing with water (20 ml), concentrating the resulting organic layer and purifying according to a silica gel column chromatography to obtain a diol substance (110 mg). Its structure was confirmed by way of NMR.

The thus obtained diol substance (110 mg), magnesium sulfate (200 mg) and benzene (10 ml) were placed in a 50 ml capacity eggplant type flask, followed by refluxing the mixture for 5 hours, removing magnesium sulfate by filtration and purifying according to silica gel column chromatography to obtain the objective 14aH-14a-methylbenzo[f]naphtho[3,2]chromene (20 mg) and keto substance (2) (50 mg). The structures of these compounds were confirmed by NMR. Further, the results of elementary analyses also accorded with the calculated values as described below.

The NMR data of the compounds are as follows:
Compound (14aH-14a-methylbenzo[f]naphtho[3,2]-chromene) expressed by the formula (1)
$^1H$ NMR $(CDCl_3)\delta=1.3$ ((s), 3H, $-CH_3$), 6.2 and 6.5 (d, each 1H, cis$-CH=CH-$), 7.0~8.0 (m, 11H, aromatic)

Compound expressed by the formula (2) (keto substance)
$^1H$ NMR $(CDCl_3)\delta=2.2$ ((s)3H, $-CH_3$), 6.3~7.4 (m, 13H, aromatic)

Photoproduct (compound corresponding to 3 in FIG. 1)
$^1H$ NMR $(CDCl_3)$ $\delta=0.9$ ((s), 3 H, $-CH_3$), 2.2 ((s), 1 H, $-CH$), 6.4 and 6.5 (d, each 1H, cis$-CH=CH-$), 7.2~7.9 (m, 10H, aromatic)

| Elemental analysis | H | C |
| --- | --- | --- |
| Calculated value | 5.44% | 89.16% |
| Observed value | 5.46% | 89.10% |

Example 2

Preparation of 14aH-14a-methylbenzo[f]naphtho[2,3]chromene

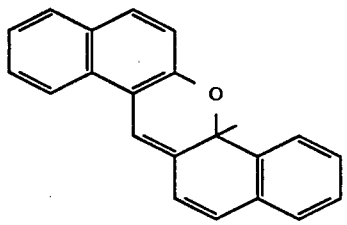

Example 1 was repeated except that 1-bromo-2-methylnaphthalene used in Example 1 was replaced by 2-bromo-1-methylnaphthalene.

Example 3

Preparation of 16aH-16a-methylbenzo[f]phenanthro[2,3-1]chromene

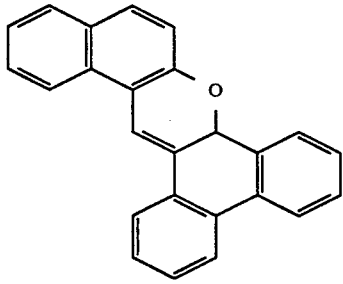

Example 1 was repeated except that 1-bromo-2-methylnaphthalene used in Example 1 was replaced by 9-bromo-10-methylphenanthrene.

Example 4

Preparation of 14aH-14a-methylbenzo[h]naphtho[3,2]chromene

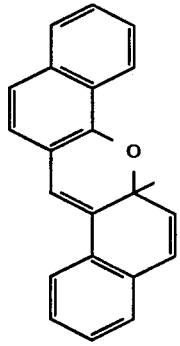

Example 1 was repeated except that 2-hydroxy-1-naphthaldehyde used in Example 1 was replaced by 1-hydroxy-2-naphthaldehyde.

Example 5

Preparation of 14aH-14a-methylbenzo[h]naphtho[2,3]chromene

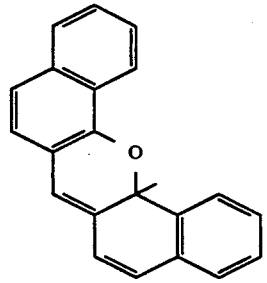

Example 1 was repeated except that 2-hydroxy-1-naphthaldehyde used in Example 2 was replaced by 1-hydroxy-2-naphthaldehyde.

Example 6

Preparation of 16ah-16a-methylbenzo[h]phenanthro[2,3-1]chromene

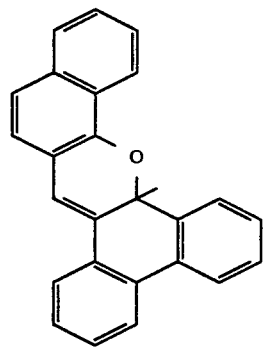

Example 1 was repeated except that 2-hydroxy-1-naphthaldehyde used in Example 3 was replaced by 1-hydroxy-2-naphthaldehyde.

Example 7

Preparation of 14aH-14a-methyldibenzo[f,h]naphtho[3,2chromene

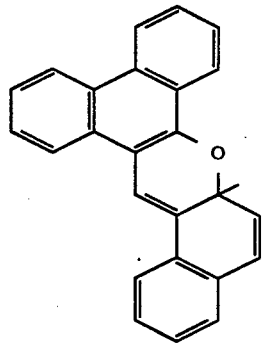

Example 1 was repeated except that 2-hydroxy-1-naphthaldehyde used in Example 1 was replaced by 9-hydroxy-10-phenanthraldehyde.

Example 8

Preparation of 14aH-14a-methyldibenzo[f,h]naphtho[2,3]chromene

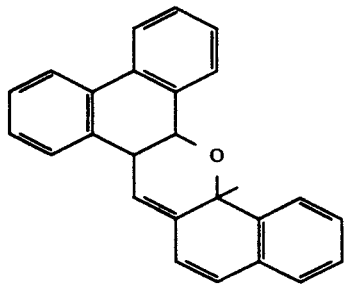

Example 1 was repeated except that 2-hydroxy-1-naphthaldehyde used in Example 2 was replaced by 9-hydroxy-10-phenanthraldehyde.

Example 9

Preparation of 16aH-16a-methyldibenzo[f,h]phenanthro[2,3-1]chromene

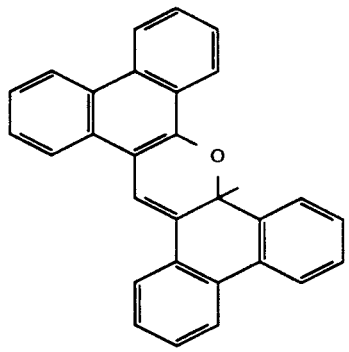

Example 1 was repeated except that 2-hydroxy-1-naphthaldehyde used in Example 3 was replaced by 9-hydroxy-10-phenanthraldehyde.

Example 10

Preparation of 13aH-13a-methylbenzo[f](benzo[b]thieno)[3,2]chromene

Example 1 was repeated except that 1-bromo-2-methylnaphthalene was replaced by 3-iodo-2-methylbenzo[b]thiophene. The NMR data of the resulting compound were as follows:

$^1$H NMR (CDCl$_3$) δ=1.7 (s, 3H, —CH$_3$), 7.0–8.2 (m, 11H, aromatic)

| Elementary analysis | | |
|---|---|---|
| | H | C |
| Calculated value | 4.68% | 79.43% |
| Observed value | 4.81% | 79.77% |

Example 11

Preparation of 13aH-12,13a-dimethylbenzo[f]indolino[3,2]chromene

Example 1 was repeated except that 1-bromo-2-methylnaphthalene used in Example 1 was replaced by 3-iodo-1,2-dimethylindole.

Example 12

Photochromic medium

A toluene solution (5 ml) of 14aH-14a-methylbenzo[f]naphtho[3,2]chromene (3 mg) prepared in Example 1 and ZEONEX 280 (tradename of product made by Nihon Zeon) (300 mg) was dripped into a Teflon vessel (inner diameter 50 mm × length 20 mm) and the solvent was gradually removed. The resulting thin film was yellow.

When the thin film was irradiated with high intensity 405 nm light, the color disappeared, whereas when the light was weak, no color change was observed even after irradiation for several hours. Further, when ultraviolet light was irradiated upon the colorless film, the film was again colored into yellow.

EFFECTIVENESS OF THE INVENTION

The compound of the present invention is a novel photochromic compound and all of its photoisomers are thermally stable, and when visible light is irradiated upon the compound, the yellow color disappeared and at that time, when the light intensity is changed, it is possible to control the color change. Thus, it is effective as optical memory element or photodisplay element which is of a rewritable type effecting non-destructive read-out. Further, since of of photoisomers of the compound of the present invention is of a three-membered structure having a large strain, it is also suitable as a material for storing solar energy. Besides the above use applications, the compound is very useful as duplicating material, lightmodulating material, photosensitive material, masking material, optical filter, toys, etc.

What we claim is:

1. A photochromic compound expressed by the formula (1)

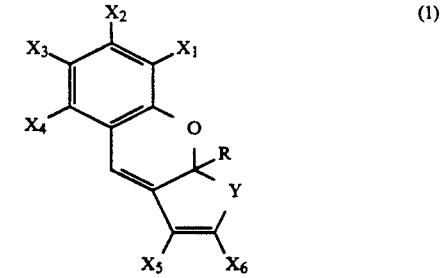

wherein R represents alkyl group, alkoxy group, perfluoroalkyl group or cyano group and $X_1$, $X_2$, $X_3$, $X_4$, $X_5$ and $X_6$ each independently represent hydrogen atom, halogen atom, alkyl group, alkoxy group, cyano group, alkanoyloxy group or alkyloxycarbonyl group, a substituted or unsubstituted benzene ring is formed by condensation between at $X_1$ and $X_2$, or/and between at $X_3$ and $X_4$, or/and between at $X_5$ and $X_6$; and Y represents $Y_1C=CY_2$, O, S, SO, SO$_2$, or NY$_3$ wherein $Y_1$ and $Y_2$ each independently represent hydrogen atom, halogen atom, alkyl group, alkoxy group, alkanoyloxy group or alkyloxycarbonyl group, or a substituted or unsubstituted benzene ring is formed by condensation between at $Y_1$ and $Y_2$ and $Y_3$ represents hydrogen atom, alkyl group, alkanoyl group, alkyloxycarbonyl group or aryl group.

2. A photochromic medium containing a photochromic compound set forth in claim 1.